(12) United States Patent
Kravtchenko et al.

(10) Patent No.: US 7,452,386 B2
(45) Date of Patent: Nov. 18, 2008

(54) COMPOSITION FOR BLEACHING AND SIMULTANEOUSLY DYEING KERATIN FIBERS, COMPRISING META-SUBSTITUTED ORTHO-NITROANILINE

(75) Inventors: Sylvain Kravtchenko, Asnieres (FR); Valérie Bonnardel, Colombes (FR)

(73) Assignee: L'Oreal S.A., Paris (FR)

( * ) Notice: Subject to any disclaimer, the term of this patent is extended or adjusted under 35 U.S.C. 154(b) by 239 days.

(21) Appl. No.: 11/293,390

(22) Filed: Dec. 5, 2005

(65) Prior Publication Data
US 2006/0191080 A1 Aug. 31, 2006

Related U.S. Application Data

(60) Provisional application No. 60/670,663, filed on Apr. 13, 2005.

(30) Foreign Application Priority Data
Dec. 3, 2004 (FR) .................................. 04 52852

(51) Int. Cl.
*A61Q 5/10* (2006.01)
(52) U.S. Cl. ...................... 8/405; 8/406; 8/411; 8/415; 8/435; 8/649; 8/667
(58) Field of Classification Search ............... 8/405, 8/406, 411, 415, 435, 649, 667
See application file for complete search history.

(56) References Cited

U.S. PATENT DOCUMENTS

| | | | |
|---|---|---|---|
| 4,185,958 A * | 1/1980 | Bugaut et al. .................. | 8/431 |
| 4,823,985 A | 4/1989 | Grollier et al. | |
| 4,863,481 A * | 9/1989 | Monnais et al. ................ | 8/414 |
| 5,026,401 A | 6/1991 | Bugaut et al. | |
| 5,688,291 A | 11/1997 | Said et al. | |
| 5,961,664 A * | 10/1999 | Anderson ...................... | 8/405 |
| 7,211,116 B2 * | 5/2007 | Kiyomine et al. .............. | 8/405 |
| 2002/0004956 A1 | 1/2002 | Rondeau | |
| 2002/0189034 A1 | 12/2002 | Kitabata et al. | |
| 2003/0000023 A9 | 1/2003 | Rondeau | |
| 2004/0181883 A1* | 9/2004 | Legrand et al. ................ | 8/405 |
| 2005/0257328 A1 | 11/2005 | Sallwey et al. | |

FOREIGN PATENT DOCUMENTS

| | | |
|---|---|---|
| DE | 203 03 559 U1 | 10/2003 |
| EP | 1 430 875 A1 | 6/2004 |
| FR | 2 586 913 A1 | 3/1987 |
| WO | WO 99/20235 | 4/1999 |
| WO | WO 02/274270 A1 | 9/2002 |
| WO | WO 03/051322 * | 6/2003 |
| WO | WO 2004/078150 A1 | 9/2004 |

OTHER PUBLICATIONS

STIC Search Report dated Sep. 19, 2007.*
English Abstract of the Patent No. WO 03/051322 A1.*
French Search Report for FR 04 52852, dated Jul. 18, 2005.

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

The present disclosure relates to a composition for bleaching and simultaneously dyeing keratin fibers, comprising at least one dye chosen from meta-substituted ortho-nitroanilines and addition salts thereof, at least one peroxygenated salt and at least one alkaline agent. The present disclosure further relates to the process for bleaching and dyeing keratin fibers using this composition, and also to the use of this composition for bleaching and simultaneously dyeing keratin fibers.

30 Claims, No Drawings

COMPOSITION FOR BLEACHING AND SIMULTANEOUSLY DYEING KERATIN FIBERS, COMPRISING META-SUBSTITUTED ORTHO-NITROANILINE

CROSS REFERENCE TO RELATED APPLICATIONS

This application claims benefit of U.S. Provisional Application No. 60/670,663, filed Apr. 13, 2005, the contents of which are incorporated herein by reference. This application also claims benefit of priority under 35 U.S.C. § 119 to French Patent Application No. 04 52852, filed Dec. 3, 2004, the contents of which are also incorporated herein by reference.

FIELD OF THE INVENTION

The present disclosure relates to a composition for bleaching and simultaneously dyeing keratin fibers, for instance human keratin fibers such as the hair, comprising at least one dye chosen from meta-substituted ortho-nitroanilines and addition salts thereof, at least one peroxygenated salt and at least one alkaline agent.

BACKGROUND OF THE INVENTION

When a person wishes to radically change the color of his or her hair, such as when he or she wishes to obtain a color lighter than his or her original color, it is often necessary to bleach and, where necessary, to dye the hair. Several methods exist for doing this.

The first method consists in using lightening products based on aqueous ammonia and hydrogen peroxide. These products may optionally contain dyes, which allow the hair to be lightened and simultaneously dyed. However, the lightening performance of these products remains limited, more particularly for applications to natural and/or dyed dark foundation colors.

The second method consists in applying to the hair a lightening composition based on peroxygenated salts such as persulfate and alkaline agents to which has been added hydrogen peroxide at the time of use, in order to obtain greater lightening. This type of product can be satisfactory and suited to dark foundation color, but may lead to only a restricted range of tints. It thus may be necessary to correct the shade obtained by applying, in a second stage, a dye product to the hair. This two-step process has the drawback of being relatively long.

To overcome this drawback, it is known practice to add dyes to these lightening products. This method can allow the hair fiber to be dyed and simultaneously bleached. Since the level of lightening is substantial, it may be suited to natural and/or dyed foundation colors. However, there is a limited number of dyes that are stable under these highly oxidative conditions, which limits the variety of tints that may be obtained. Moreover, this instability may be reflected by a more or less rapid change in the tint during application, which may lead to inconsistent results.

Moreover, the color-fastness of these dyes with respect to external agents, such as light and shampoo, may not be satisfactory.

Direct dyes of anthraquinone, azo, triarylmethane, thiazine, quinone and nitro type, which are stable in these highly oxidative media, have been proposed in U.S. Pat. No. 5,688,291, International Patent Application Publication No. WO 02/074 270, and German Patent No. DE 203 03 559. However, these dyes are unsatisfactory in terms of chromaticity, color-fastness and stability during the application time.

Thus, there is a need in the art for novel compositions for bleaching and simultaneously dyeing keratin fibers, such as human keratin fibers including the hair, which are particularly suitable for dark foundation colors, which show good stability over time and which allow chromatic and color-fast colorations to be obtained.

DETAILED DESCRIPTION OF THE INVENTION

Accordingly, the present disclosure relates to novel compositions for bleaching and simultaneously dyeing keratin fibers, comprising:
at least one dye chosen from meta-substituted ortho-nitroanilines and the addition salts thereof;
at least one peroxygenated salt; and
at least one alkaline agent.

The compositions in accordance with the present disclosure are particularly suitable for bleaching and simultaneously dyeing dark hair. They show improved stability over time and allow a chromatic coloration to be obtained. Furthermore, with suitable concentrations of at least one dye according to the present disclosure, pastel tints may be obtained.

This coloration is resistant to the various attacking factors to which hair may be subjected, such as shampoo, rubbing, light, bad weather, sweat and permanent reshaping operations. It is also powerful, aesthetic and, furthermore, sparingly selective, i.e., it produces only small differences between different parts of a hair or of a head of hair that are differently sensitized.

The present disclosure also relates to a process for bleaching and simultaneously dyeing keratin fibers, using the composition in accordance with the present disclosure, and also multi-compartment devices for implementing this process.

The present disclosure still further relates to the use of the composition in accordance with the present disclosure for bleaching and simultaneously dyeing keratin fibers.

As used herein, the term "meta-substituted ortho-nitroaniline" is understood to mean an ortho-nitroaniline optionally substituted on the amino group, which has at least one substituent on the benzene ring meta to this amino group.

According to one embodiment of the present disclosure, the at least one meta-substituted ortho-nitroaniline that is used in the context of the present disclosure is chosen from the compounds of formula (I):

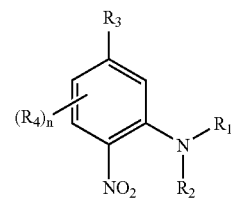

wherein:
n is an integer ranging from 0 to 3;
$R_1$ and $R_2$, which may be identical or different, are chosen from:
hydrogen atoms;
alkyl radicals;
hydroxyalkyl radicals;
aminoalkyl radicals;
haloalkyl radicals;
optionally substituted aryl radicals;

$R_1$ and $R_2$ together may form, with the nitrogen atom to which they are attached, a saturated or unsaturated, 5- or 6-membered heterocycle optionally comprising at least one additional heteroatom and optionally substituted;

$R_3$ and $R_4$, which may be identical or different, are chosen from:
alkyl radicals;
hydroxyalkyl radicals;
aminoalkyl radicals;
haloalkyl radicals;
amino radicals;
mono(alkyl)amino and di(alkyl)amino radicals;
mono(hydroxyalkyl)amino and di(hydroxyalkyl)amino radicals;
N,N-(alkyl)(hydroxyalkyl)amino radicals;
halogen atoms;
hydroxyl radicals;
alkoxy radicals;
hydroxyalkoxy radicals; and
carboxyalkoxy radicals.

As used herein, the term "alkyl radical" (alk) is understood to mean a linear or branched radical comprising from 1 to 6 carbon atoms, for example a methyl, ethyl, n-propyl, isopropyl, n-butyl or tert-butyl radical. Also as used herein, an alkoxy radical is understood to mean a radical alk-O—, and a monoalkylamino or dialkylamino radical is a radical $(alk)_n$N— with n=1 or 2, the alkyl radical being as defined above.

A substituted alkyl radical can be a monosubstituted or polysubstituted alkyl radical. For example, a hydroxyalkyl radical is an alkyl radical that may be substituted with at least one hydroxyl group, an aminoalkyl radical is an alkyl radical that may be substituted with at least one amino group, a haloalkyl radical is an alkyl radical that may be substituted with at least one halo group, and a carboxyalkyl radical is an alkyl radical that may be substituted with at least one carboxyl group.

As used herein, a halo radical is understood to mean a halogen atom chosen from chlorine, bromine, iodine and fluorine.

As used herein, the term "aryl radical" is understood to mean a carbon-based radical derived from fused or non-fused benzene-based compounds comprising from 6 to 30 carbon atoms, for example a phenyl, anthracenyl or naphthyl radical.

A saturated or unsaturated 5- or 6-membered heterocycle optionally comprising at least one additional heteroatom may be, for example, a pyrrolidine ring, a piperidine ring, a piperazine ring or a morpholine ring.

In all the above meanings, when a group is substituted, it can be mono- or polysubstituted and the substituents can be chosen from halo, hydroxyl, alkyl, hydroxyalkyl, haloalkyl, alkoxy, amino, mono(alkyl)amino, di(alkyl)amino, mono(hydroxyalkyl)amino, di(hydroxyalkyl)amino, and carboxyl radicals. For example, the p-methoxyphenyl radical can be a substituted aryl radical.

According to one embodiment of the present disclosure, n is chosen from 0 or 1.

According to another embodiment of the present disclosure, $R_1$ and $R_2$, which may be identical or different, are chosen from hydrogen atoms; alkyl radicals; aminoalkyl radicals; and hydroxyalkyl radicals. By way of non-limiting example, in one embodiment, $R_1$ and $R_2$ can be chosen from hydrogen atoms; methyl radicals; β-aminoethyl radicals; and β-hydroxyethyl radicals.

According to still another embodiment of the present disclosure, $R_1$ and/or $R_2$ are chosen from hydrogen atoms.

According to one embodiment of the present disclosure, $R_3$ and $R_4$, which may be identical or different, are chosen from alkyl radicals; amino radicals; mono(hydroxyalkyl)amino and di(hydroxyalkyl)amino radicals; halogen atoms; hydroxyl radicals; alkoxy radicals; hydroxyalkoxy radicals; and carboxyalkoxy radicals. By way of non-limiting example, $R_3$ and $R_4$ can also be chosen from methyl radicals; amino radicals; β-hydroxyethylamino radicals; chlorine atoms; hydroxyl radicals; methoxy radicals; β-hydroxyethyloxy radicals; β,γ-dihydroxypropyloxy radicals; and carboxymethyloxy radicals.

According to another embodiment of the present disclosure, $R_3$ is chosen from optionally substituted amino radicals.

As non-limiting examples of meta-substituted ortho-nitroanilines that are useful in the context of the present disclosure, non-limiting mention may be made of 4-nitro-meta-phenylenediamine; 1-(β-hydroxyethyloxy)-3-methylamino-4-nitrobenzene; 1-carboxymethyloxy-3-methylamino-4-nitrobenzene; 1-methylamino-2-nitro-5-(β,γ-dihydroxypropyl)oxybenzene; 1-amino-2-nitro-4-hydroxy-5-methylbenzene; 1-amino-3-methyl-4-(β-hydroxyethyl)amino-6-nitrobenzene; 1-methoxy-3-(β-aminoethylamino)-4-nitrobenzene; 1,5-di(β-hydroxyethylamino)-2-nitro-4-chlorobenzene; and 1-amino-2-nitro-4-(β-hydroxyethylamino)-5-chlorobenzene.

For instance, in one embodiment of the present disclosure, the at least one meta-substituted ortho-nitroaniline that is used in the context of the present disclosure is chosen from 1,5-di(β-hydroxyethylamino)-2-nitro-4-chlorobenzene, also known as HC Yellow 10 or Imexine FAH, and the addition salts thereof.

The addition salts of the meta-substituted ortho-nitroanilines that may be used in the context of the present disclosure can be chosen from, for example, the addition salts with an organic or mineral base, such as the salts of alkali metals or of alkaline-earth metals and the salts of organic amines such as alkanolamines. In one embodiment of the present disclosure, sodium salts are used.

The at least one meta-substituted ortho-nitroanilines and/or addition salts thereof in the composition in accordance with the present disclosure can be present in an amount ranging from 0.0001% to 10% by weight, for instance from 0.001% to 8%, such as from 0.01% to 5% by weight, relative to the total weight of the composition.

Among the peroxygenated salts that can be used according to the present disclosure, non-limiting mention can be made of, for example, alkali metal and/or alkaline-earth metal persulfates, perborates, percarbonates and/or peroxides, and mixtures thereof. Persulfates and mixtures thereof, and more preferentially sodium persulfate, potassium persulfate and ammonium persulfate, and mixtures thereof, are used in one embodiment.

The at least one peroxygenated salt in the composition in accordance with the present disclosure can be present in an amount ranging from 10% to 70% by weight, such as ranging from 20% to 60% by weight, relative to the total weight of the composition.

The at least one alkaline agent can be chosen, for example, from urea, ammonium salts, for instance ammonium chloride, ammonium sulfate, ammonium phosphate, ammonium nitrate, silicates, phosphates and/or carbonates of alkali metals and/or of alkaline-earth metals such as lithium, sodium, potassium, magnesium, calcium and barium. For instance, the at least one alkaline agent can be chosen from ammonium chloride, silicates and carbonates.

The at least one alkaline agent in the composition in accordance with the present disclosure can range from 0.01% to 40% by weight, such as from 0.1% to 30% by weight, relative to the total weight of the composition.

The composition in accordance with the present disclosure may be in the form of a powder or a paste. In one embodiment, the composition of the present disclosure is in the form of a paste.

When the composition in accordance with the present disclosure is in the form of a paste, it also comprises at least one inert organic liquid phase.

As used herein, the term "liquid phase" is understood to mean any phase capable of flowing at room temperature, ranging from 15° C. to 40° C., and at atmospheric pressure, under the action of its own weight.

Non-limiting examples of inert liquid phases that may be mentioned include the polydecenes of formula $C_{10n}H_{[(20n)+2]}$ in which n ranges from 3 to 9, such as from 3 to 7, esters of fatty alcohols, esters of fatty acids, $C_{12}$-$C_{24}$ fatty acid esters, $C_{12}$-$C_{24}$ fatty acid esters of sugars, $C_{12}$-$C_{24}$ fatty acid diesters of sugars, cyclic ethers, cyclic esters, silicone oils, mineral oils, and plant oils, and mixtures thereof.

The compounds of formula $C_{10n}H_{[(20n)+2]}$ with n ranging from 3 to 9 correspond to the name "polydecene" of the CTFA dictionary 7th edition, 1997 of the Cosmetic, Toiletry and Fragrance Association, USA, and also to the same INCI name in USA and Europe. These are products of hydrogenation of poly-1-decenes.

Among these compounds, in one embodiment of the present disclosure, the ones that are used are those in which n ranges from 3 to 7.

Non-limiting examples that may be mentioned include the product sold under the name Silkflo® 366 NF Polydecene by the company Amoco Chemical, and those sold under the name Nexbase® 2002 FG, 2004 FG, 2006 FG and 2008 FG by the company Fortum.

For the esters of fatty alcohols or of fatty acids, non-limiting examples that may be mentioned include:

esters of linear or branched, saturated lower $C_3$-$C_6$ monoalcohols with $C_{12}$-$C_{24}$ monofunctional fatty acids, these fatty acids possibly being linear or branched, and saturated or unsaturated, and chosen for example from oleates, laurates, palmitates, myristates, behenates, cocoates, stearates, linoleates, linolenates, caprates and arachidonates, or mixtures thereof, such as oleopalmitates, oleostearates and palmitostearates. Among these esters, further non-limiting mention may be made of isopropyl palmitate, isopropyl myristate and octyldodecyl stearate;

esters of linear or branched $C_3$-$C_8$ monoalcohols with $C_8$-$C_{24}$ difunctional fatty acids, these fatty acids possibly being linear or branched, and saturated or unsaturated, for instance the isopropyl diester of sebacic acid, also known as diisopropyl sebacate;

esters of linear or branched $C_3$-$C_8$ monoalcohols with $C_2$-$C_8$ difunctional fatty acids, these fatty acids possibly being linear or branched, and saturated or unsaturated, for instance dioctyl adipate and dicaprylyl maleate; and esters of a trifunctional acid, for instance triethyl citrate.

For the $C_{12}$-$C_{24}$ fatty acid esters and diesters of sugars, as used herein, the term "sugar" is understood to mean compounds comprising several alcohol functional groups, with or without an aldehyde or ketone functional group, and which comprise at least four carbon atoms. These sugars may be monosaccharides, oligosaccharides or polysaccharides.

As sugars that may be used according to the present disclosure, non-limiting mention may be made, for example, of sucrose (or saccharose), glucose, galactose, ribose, fucose, maltose, fructose, mannose, arabinose, xylose and lactose, and derivatives thereof, for example alkyl derivatives, such as methyl derivatives, for instance methylglucose.

The fatty acid esters of sugars that may be used according to the present disclosure may be chosen for example, from the group comprising esters or mixtures of esters of sugars described above and of linear or branched, saturated or unsaturated $C_{12}$-$C_{24}$ fatty acids.

The esters may be chosen from mono-, di-, tri-, tetraesters and polyesters, and mixtures thereof.

These esters may be chosen, by way of non-limiting example, from oleates, laurates, palmitates, myristates, behenates, cocoates, stearates, linoleates, linolenates, caprates and arachidonates, or mixtures thereof, for instance mixed oleo-palmitates, oleo-stearates or palmito-stearates.

In one embodiment of the present disclosure, mono- and diesters are used, such as sucrose, glucose or methylglucose mono- or dioleates, stearates, behenates, oleopalmitates, linoleates, linolenates or oleostearates.

Mention may be made, for example, of the product sold under the name Glucate® DO by the company Amerchol, which is a methylglucose dioleate.

Mention may also be made, as non-limiting examples of esters or of mixtures of esters of sugar and of fatty acid, of:

the products sold under the names F160, F140, F110, F90, F70 and SL40 by the company Crodesta, respectively denoting sucrose palmito-stearates formed from 73% monoester and 27% diester and triester, 61% monoester and 39% diester, triester and tetraester, 52% monoester and 48% diester, triester and tetraester, 45% monoester and 55% diester, triester and tetraester, and 39% monoester and 61% diester, triester and tetraester, and sucrose monolaurate;

the products sold under the name Ryoto Sugar Esters, for example referenced B370 and corresponding to sucrose behenate formed from 20% monoester and 80% di-triester-polyester;

sucrose mono-di-palmito-stearate sold by the company Goldschmidt under the name Tegosofte® PSE.

For the cyclic ethers and cyclic esters, mention may be made of γ-butyrolactone, dimethyl isosorbide or diisopropyl isosorbide.

At least one silicone oil may also be used as inert organic liquid phase.

For example, the silicone oils that are suitable are liquid, non-volatile silicone fluids with a viscosity of less than or equal to 10,000 mPa.s at 25° C., the viscosity of the silicones being measured according to ASTM standard 445 Appendix C.

Silicone oils are defined in greater detail in Walter Noll's "Chemistry and Technology of Silicones" (1968)-Academic Press.

Among the silicone oils that may be used according to the present disclosure, examples include the silicone oils sold under the names DC-200 Fluid—5 mPa.s, DC-200 Fluid—20 mpa.s, DC-200 Fluid—350 mPa.s, DC-200 Fluid—1,000 mPa.s and DC-200 Fluid—10,000 mPa.s by the company Dow Corning.

At least one mineral oil may also be used as inert organic liquid phase, for instance liquid paraffin.

At least one plant oil may also be suitable for use, such as avocado oil, olive oil or liquid jojoba wax.

In one embodiment of the present disclosure, the at least one inert organic liquid phase is chosen from the polydecenes of formula $C_{10n}H_{[(20n)+2]}$ in which n ranges from 3 to 9, such as from 3 to 7, esters of fatty alcohols, esters of fatty acids, and mixtures thereof.

According to another embodiment of the present disclosure, the at least one inert organic liquid phase is present in an amount ranging from 5% to 60% by weight, for instance, from 10% to 50% by weight, such as from 15% to 45% by weight, relative to the weight of the anhydrous paste.

According to still another embodiment, the composition in accordance with the present disclosure is anhydrous.

As used herein, a composition is understood to be anhydrous when it has a water content of less than 1% by weight, such as less than 0.5% by weight, relative to the total weight of the composition.

According to yet another embodiment, the composition in accordance with the present disclosure also comprises hydrogen peroxide.

The pH of the composition comprising hydrogen peroxide in accordance with the present disclosure can range from 3 to 11, such as from 7 to 11.

The composition in accordance with the present disclosure may also comprise at least one adjuvant conventionally used in cosmetics.

The composition in accordance with the present disclosure may thus comprise at least one adjuvant chosen from mineral and organic thickeners, such as associative and non-associative, anionic, cationic, nonionic and amphoteric thickening polymers; fillers such as clays; binders such as vinylpyrrolidone; lubricants, for instance polyol stearates and/or alkali metal and/or alkaline-earth metal stearates; hydrophilic and/or hydrophobic silicas; pigments; dyes other than those of the present disclosure; matting agents, for instance titanium oxides;anionic, nonionic, cationic, amphoteric and zwitterionic surfactants; antioxidants; penetrants; sequestrants; buffers; dispersants; film-forming agents; preserving agents; opacifiers; vitamins; fragrances; anionic, cationic, nonionic, amphoteric and zwitterionic polymers; ceramides; and conditioning agents, for instance volatile and/or non-volatile, modified and/or unmodified silicones.

When the composition in accordance with the present disclosure comprises hydrogen peroxide, it may also comprise at least one agent for controlling the release of oxygen, such as magnesium carbonate or oxide.

The at least one adjuvant and at least one agent for controlling the release of oxygen as defined above may be present in an amount for each ranging from 0.01% to 40% by weight, such as from 0.1% to 30% by weight, relative to the total weight of the composition.

Needless to say, a person skilled in the art will take care to select this or these optional additional component(s) such that the beneficial properties intrinsically associated with the composition in accordance with the present disclosure are not, or are not substantially, adversely affected by the envisaged addition(s).

The process of bleaching and of simultaneous dyeing keratin fibers in accordance with the present disclosure comprises applying to the keratin fibers a composition comprising hydrogen peroxide in accordance with the present disclosure as defined above.

One embodiment of the present disclosure is also a multi-compartment device, comprising at least two compositions, the mixing of which leads to a composition comprising hydrogen peroxide as defined above.

According to another embodiment of the present disclosure, the device in accordance with the present disclosure comprises at least one first compartment comprising at least one composition (A) comprising, in a suitable dyeing medium, at least one dye as defined above, at least one second compartment comprising at least one anhydrous composition (B) comprising at least one peroxygenated salt and at least one alkaline agent as defined above, and at least one third compartment comprising an aqueous hydrogen peroxide composition (E).

According to yet another embodiment of the present disclosure, the device comprises at least one first compartment comprising at least one anhydrous composition (C) comprising at least one dye as defined above, at least one peroxygenated salt and at least one alkaline agent as defined above, and at least one second compartment comprising at least one aqueous hydrogen peroxide composition (E).

According to still another embodiment of the present disclosure, the device comprises at least one first compartment that comprises at least one anhydrous composition (B) comprising at least one peroxygenated salt and at least one alkaline agent as defined above, and at least one second compartment comprising at least one composition (D) comprising, in a suitable dyeing medium, at least one dye as defined above and hydrogen peroxide.

The suitable dyeing medium for compositions (A) and (D) can consist of water or can comprise a mixture of water and of at least one organic solvent to dissolve the compounds that are not sufficiently water-soluble. Non-limiting examples of organic solvents that may be mentioned include $C_1$-$C_4$ lower alkanols such as ethanol and isopropanol; glycerol; glycols and glycol ethers, for instance 2-butoxyethanol, propylene glycol, propylene glycol monomethyl ether, and also aromatic alcohols, for instance benzyl alcohol or phenoxyethanol, and mixtures thereof.

The at least one solvent may be present in an amount ranging from 1% to 40% by weight, such as from 5% to 30% by weight, relative to the total weight of the dye composition.

The at least one composition (A), also known as the "booster," may be formulated at acidic, neutral or alkaline pH, the pH ranging, for example, from 3 to 12, such as from 4 to 11.

In one embodiment, the at least one composition (D) has a pH of less than 7, the acidic pH ensuring the stability of the hydrogen peroxide in this composition.

The compositions (A) and (D) may be in various forms, such as in the form of liquids, creams or gels, or in any other form that is suitable for dyeing keratin fibers.

The anhydrous compositions (B) and (C) may be in the form of powder or paste. When in the form of paste, they also comprise an inert organic liquid phase as defined above.

In one embodiment, the at least one aqueous hydrogen peroxide composition (E) has a pH of less than 7, the acidic pH ensuring the stability of the hydrogen peroxide in this composition.

The compositions (A), (B), (C), (D) and (E) may also comprise at least one adjuvant conventionally used in cosmetics, such as those described above.

The compositions (E) and (D) may also comprise at least one agent for controlling the release of oxygen, as defined above.

The device in accordance with the present disclosure may be equipped with an applicator for applying the desired mixture to the hair, such as the devices described in French Patent No. FR-2 586 913.

Using this device, it is possible to bleach and simultaneously dye keratin fibers by means of a process in accordance with the disclosure as defined above.

One embodiment of the present disclosure is also the use, for bleaching and simultaneously dyeing keratin fibers, of a composition in accordance with the present disclosure as defined above.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

The example that follows serves to illustrate the present disclosure without, however, being limiting in nature.

EXAMPLE

HC Yellow 10 was dissolved in an aqueous-alcoholic solution (80/20) to a concentration of 3.5 g %. Booster (composition A) was thus obtained.

This solution was added just before use to a mixture of Platine Precision (composition B) powder comprising 51.5% of a mixture of sodium, potassium and magnesium persulfates in the presence of 4.2% of a mixture of sodium metasilicate and ammonium chloride with an oxidizing agent (composition E) consisting of a 40-volumes aqueous hydrogen peroxide composition. The proportions of the bleaching powder (B)/oxidizing agent (E)/booster (A) mixture were, respectively, 1/2/0.5.

A portion of this mixture was applied immediately to a 1 g lock of natural hair comprising 90% white hairs, and also to a lock of 2.7 g of natural chestnut-brown hair.

The remainder of this mixture was applied 20 minutes later to a lock of 1 g of natural hair comprising 90% white hairs and also to a lock of 2.7 g of natural chestnut-brown hair.

In all cases, the conditions were identical. The bath ratio was equal to 10.

After a leave-on time of 30 minutes, the locks were rinsed and then shampooed, rinsed again and dried.

The results are given in the table below.

TINTS OBTAINED AFTER APPLYING THE COMPOSITIONS OF THE PRESENT DISCLOSURE

|  | Natural hair comprising 90% white hairs | Natural chestnut-brown hair |
| --- | --- | --- |
| Immediate application of the mixture | Intense golden | Slightly coppery golden |
| Delayed application of the mixture | Intense golden | Slightly coppery golden |

The natural hair comprising 90% white hairs was used here to demonstrate any possible change in tint.

It was found that the same tint was obtained when the mixture was applied immediately and when its application was delayed.

These results show that the compositions in accordance with the present disclosure are stable over time.

What is claimed is:

1. A composition for bleaching and simultaneously dyeing keratin fibers, comprising:

at least one dye chosen from meta-substituted ortho-nitroanilines and the addition salts thereof, with the proviso that the meta-substituted ortho-nitroaniline is not 4-nitro-meta-phenylenediamine;

at least one peroxygenated salt; and at least one alkaline agent.

2. The composition according to claim 1, wherein the at least one meta-substituted ortho-nitroaniline is chosen from the compounds of formula (I):

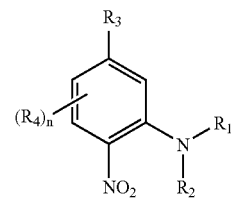

wherein:

n is an integer ranging from 0 to 3;

$R_1$ and $R_2$, which may be identical or different, are chosen from:

hydrogen atoms;

alkyl radicals;

hydroxyalkyl radicals;

aminoalkyl radicals;

haloalkyl radicals; and optionally substituted aryl radicals;

R1 and $R_2$ together may form, with the nitrogen atom to which they are attached, a saturated or unsaturated, 5- or 6-membered heterocycle optionally comprising at least one additional heteroatom and optionally substituted;

$R_3$ and $R_4$, which may be identical or different, are chosen from:

alkyl radicals;

hydroxyalkyl radicals;

aminoalkyl radicals;

haloalkyl radicals;

amino radicals;

mono(alkyl)amino and di(alkyl)amino radicals;

mono(hydroxyalkyl)amino and di(hydroxyalkyl)amino radicals;

N,N-(alkyl)(hydroxyalkyl)amino radicals;

halogen atoms;

hydroxyl radicals;

alkoxy radicals;

hydroxyalkoxy radicals; and carboxyalkoxy radicals;

with the proviso that when n=0, then $R_3$ is not $NH_2$.

3. The composition according to claim 2, wherein n is equal to 0 or 1.

4. The composition according to claim 2, wherein $R_1$ and $R_2$, which may be identical or different, are chosen from hydrogen atoms; alkyl radicals; aminoalkyl radicals; and hydroxyalkyl radicals.

5. The composition according to claim 4, wherein $R_1$ and $R_2$, which may be identical or different, are chosen from hydrogen atoms; methyl radicals; β-aminoethyl radicals; and β-hydroxyethyl radicals.

6. The composition according to claim 2, wherein $R_1$ and/or $R_2$ is chosen from hydrogen atoms.

7. The composition according to claim 2, wherein $R_3$ and $R_4$, which may be identical or different, are chosen from alkyl radicals; amino radicals; mono(hydroxyalkyl)amino radicals; di(hydroxyalkyl)amino radicals; halogen atoms; hydroxyl radicals; alkoxy radicals; hydroxyalkoxy radicals; and carboxyalkoxy radicals.

8. The composition according to claim 7, wherein $R_3$ and $R_4$, which may be identical or different, are chosen from methyl radicals; amino radicals; β-hydroxyethylamino radicals; chlorine atoms; hydroxyl radicals; methoxy radicals; β-hydroxyethyloxy radicals; β, γ-dihydroxypropyloxy radicals; and carboxymethyloxy radicals.

9. The composition according to claim 8, wherein $R_3$ is chosen from optionally substituted amino radicals.

10. The composition according to claim 1, wherein the at least one meta-substituted ortho-nitroaniline is chosen from 1-(β-hydroxyethyloxy)-3-methylamino-4-nitrobenzene; 1-carboxymethyloxy-3-methylamino-4-nitrobenzene; 1-methylamino-2-nitro-5-(β,γ-dihydroxypropy)oxybenzene; 1-amino-2-nitro-4-hydroxy-5-methylbenzene; 1-amino-3-methyl-4-(β-hydroxyethyl)amino-6-nitrobenzene; 1-methoxy-3-(β-aminoethylamino)-4-nitrobenzene; 1,5-di(β-hydroxyethylamino)-2-nitro-4-chlorobenzene; and 1-amino-2-nitro-4-(β-hydroxyethylamino)-5-chlorobenzene.

11. The composition according to claim 10, wherein the at least one meta-substituted ortho-nitroaniline is chosen from 1,5-di(β-hydroxyethylamino)-2-nitro-4-chlorobenzene and the addition salts thereof.

12. The composition according to claim 10, wherein the at least one dye is chosen from the sodium salts of meta-substituted ortho-nitroanilines, and mixtures thereof.

13. The composition according to claim 1, wherein the at least one meta-substituted ortho-nitroanilines and/or addition salts thereof is present in an amount ranging from 0.0001% to 10% by weight, relative to the total weight of the composition.

14. The composition according to claim 1, wherein the at least one peroxygenated salt is chosen from alkali metal and alkaline-earth metal persulfates, perborates, percarbonates, and peroxides.

15. The composition according to claim 14, wherein the at least one peroxygenated salt is chosen from persulfates.

16. The composition according to claim 15, wherein the at least one peroxygenated salt is chosen from sodium persulfate, potassium persulfate and ammonium persulfate.

17. The composition according to claim 1, wherein the at least one peroxygenated salt is present in an amount ranging from 10% to 70% by weight, relative to the total weight of the composition.

18. The composition according to claim 1, wherein the at least one alkaline agent is chosen from urea, ammonium chloride, ammonium sulfate, ammonium phosphate, ammonium nitrate, alkali metal silicates, alkaline-earth metal silicates, phosphates and carbonates.

19. The composition according to claim 1, wherein the at least one alkaline agent is present in an amount ranging from 0.01% to 40% by weight, relative to the total weight of the composition.

20. The composition according to claim 1, further comprising at least one inert organic liquid phase.

21. The composition according to claim 20, wherein the at least one inert organic liquid phase is chosen from the polydecenes of formula $C_{10n}H_{[(20n)+2]}$ wherein n ranges from 3 to 9, esters of fatty alcohols, esters of fatty acids, $C_{12}$-$C_{24}$ fatty acid esters of sugars, $C_{12}$-$C_{24}$ fatty acid diesters of sugars, cyclic ethers, cyclic esters, silicone oils, mineral oils, and plant oils.

22. The composition according to claim 21, in which the at least one inert organic liquid phase is chosen from the polydecenes of formula $C_{10n}H_{[(20n)+2]}$ wherein n ranges from 3 to 9, and esters of fatty alcohols, and esters of fatty acids.

23. The composition according to claim 20, wherein the at least one inert organic liquid phase is present in an amount ranging from 5% to 60% by weight, relative to the total weight of the composition.

24. The composition according to claim 1, wherein the composition is anhydrous.

25. The composition according to claim 1, further comprising hydrogen peroxide.

26. A process for bleaching and simultaneously dyeing keratin fibers, comprising applying to the keratin fibers a composition comprising:
  at least one dye chosen from meta-substituted ortho-nitroanilines and the addition salts thereof, with the proviso that the meta-substituted ortho-nitroaniline is not 4-nitro-meta-phenylenediamine;
  at least one peroxygenated salt; and
  at least one alkaline agent.

27. A multi-compartment device, comprising at least two compositions, the mixing of which leads to a composition comprising:
  at least one dye chosen from meta-substituted ortho-nitroanilines and the addition salts thereof, with the proviso that the meta-substituted ortho-nitroaniline is not 4-nitro-meta-phenylenediamine;
  at least one peroxygenated salt; and
  at least one alkaline agent.

28. A multi-compartment device comprising at least one first compartment containing at least one composition (A) comprising, in a suitable dyeing medium, at least one dye chosen from meta-substituted ortho-nitroanilines and the addition salts thereof, with the proviso that the meta-substituted ortho-nitroaniline is not 4-nitro-meta-phenylenediamine, at least one second compartment containing at least one anhydrous composition (B) comprising at least one peroxygenated salt, and at least one alkaline agent, and at least one third compartment containing at least one aqueous hydrogen peroxide composition (E).

29. A multi-compartment device comprising at least one first compartment containing at least one anhydrous composition (C) comprising at least one dye chosen from meta-substituted ortho-nitroanilines and the addition salts thereof, with the proviso that the meta-substituted ortho-nitroaniline is not 4-nitro-meta-phenylenediamine, at least one peroxygenated salt, and at least one alkaline agent, and at least one second compartment containing at least one aqueous hydrogen peroxide composition (E).

30. A multi-compartment device comprising at least one first compartment containing at least one anhydrous composition (B) comprising at least one peroxygenated salt, and at least one alkaline agent, and at least one second compartment containing at least one composition (D) comprising, in a suitable dyeing medium, at least one dye chosen from meta-substituted ortho-nitroanilines and the addition salts thereof and hydrogen peroxide, with the proviso that the meta-substituted ortho-nitroaniline is not 4-nitro-meta-phenylenediamine.

\* \* \* \* \*

UNITED STATES PATENT AND TRADEMARK OFFICE
CERTIFICATE OF CORRECTION

PATENT NO. : 7,452,386 B2
APPLICATION NO. : 11/293390
DATED : November 18, 2008
INVENTOR(S) : Sylvain Kravtchenko et al.

It is certified that error appears in the above-identified patent and that said Letters Patent is hereby corrected as shown below:

In claim 8, column 11, lines 8-9, "β, γ-dihydroxypropyloxy" should read --β,γ-dihydroxypropyloxy--.

In claim 10, column 11, lines 15-16, "1-methylamino-2-nitro-5-(β,γ-dihydroxypropy) oxybenzene;" should read --1-methylamino-2-nitro-5-(β,γ-dihydroxypropyl) oxybenzene;--.

In claim 10, column 11, lines 20-21, "1 -amino-2-nitro-4-(β-hydroxyethylamino)-5-chlorobenzene." should read --1-amino-2-nitro-4-(β-hydroxyethylamino)-5-chlorobenzene.--.

In claim 11, column 11, line 24, "1.5-di(β-hydroxyethylamino)-2-nitro-4-chlorobenzene" should read --1,5-di(β-hydroxyethylamino)-2-nitro-4-chlorobenzene--.

Signed and Sealed this

Twenty-seventh Day of January, 2009

JOHN DOLL
*Acting Director of the United States Patent and Trademark Office*